United States Patent [19]
Reffner et al.

[11] Patent Number: 5,581,085
[45] Date of Patent: Dec. 3, 1996

[54] INFRARED MICROSPECTROMETER ACCESSORY

[75] Inventors: John A. Reffner, Stamford; William T. Wihlborg, Milford, both of Conn.

[73] Assignee: Spectra-Tech, Inc., Shelton, Conn.

[21] Appl. No.: 399,197

[22] Filed: Mar. 6, 1995

[51] Int. Cl.$^6$ .................................................. G01N 21/35
[52] U.S. Cl. .............................. 250/339.07; 250/339.05; 250/339.06; 250/339.11; 250/339.12
[58] Field of Search ................... 250/339.11, 339.07, 250/339.06, 339.05, 339.12

[56] References Cited

U.S. PATENT DOCUMENTS

| | | |
|---|---|---|
| 3,370,502 | 2/1968 | Wilks . |
| 4,595,833 | 6/1986 | Sting . |
| 4,758,088 | 6/1988 | Doyle . |
| 4,810,077 | 3/1989 | Sting . |
| 4,843,242 | 6/1989 | Doyle . |
| 4,844,617 | 7/1989 | Kelderman et al. . |
| 4,852,995 | 8/1989 | Cordier et al. . |
| 4,877,960 | 10/1989 | Messerschmidt et al. . |
| 4,878,747 | 11/1989 | Sting et al. . |
| 4,922,104 | 5/1990 | Eguchi et al. ............... 250/339.08 |
| 5,019,715 | 5/1991 | Sting et al. ................. 250/571 |
| 5,093,580 | 3/1992 | Sting . |
| 5,200,609 | 4/1993 | Sting et al. . |
| 5,216,244 | 6/1993 | Esaki et al. . |
| 5,225,678 | 7/1993 | Messerschmidt . |
| 5,278,413 | 1/1994 | Yamaguchi et al. . |
| 5,434,411 | 7/1995 | Miyahara et al. ............. 250/339.07 |

FOREIGN PATENT DOCUMENTS

| | | |
|---|---|---|
| 0426040A1 | 8/1991 | European Pat. Off. . |
| 0493777A2 | 8/1992 | European Pat. Off. . |
| 5-164972 | 6/1993 | Japan .................................. 250/330 |
| WO95/317111 | 11/1995 | WIPO . |

OTHER PUBLICATIONS

"Design and Performance of an Infrared Microscope Attachment," Coates et al., *Journal of the Optical Society of America*, vol. 43, No. 11, pp. 984–989, Nov. 1953.
"Optical Techniques for Industrial Inspection," P. Cielo, *Academic Press, Inc.*, San Diego, 1988.
*Das Mikroskop*, Leica Mikroskopie and Systems GmbH, Germany, Jul. 1993.
*Lympus BS*, Olympus Optical Co., Ltd., Tokyo, Japan, Mar. 1994.

*Primary Examiner*—Constantine Hannaher
*Attorney, Agent, or Firm*—Calfee, Halter & Griswold

[57] ABSTRACT

This invention is an apparatus and method for infrared spectroscopic or radiometric analysis of microscopic samples of solids or liquids, combining external- or internal-reflection spectroscopy with visible-radiant energy viewing of microscopic samples by integrated video microscopy. This is an accessory to Fourier-transform-infrared spectrometers for the chemical analysis of microscopic samples in specular, diffuse, reflection-absorption (transflection), or internal-reflection spectroscopy. This apparatus combines an all-reflective, infinity-corrected optical system with an integrated, dedicated, video viewing system. The magnification optic is an all-reflecting optic designed to focus a collimated beam of radiant energy onto the sample, collect the reflected radiant energy, and (through the appropriate optics) present that energy to a detector means for spectral analysis. The modified Schwarzchild all-reflecting objective lens also provides a magnified image of the microscopic sample, which is detected by an integrated video imaging system.

21 Claims, 10 Drawing Sheets

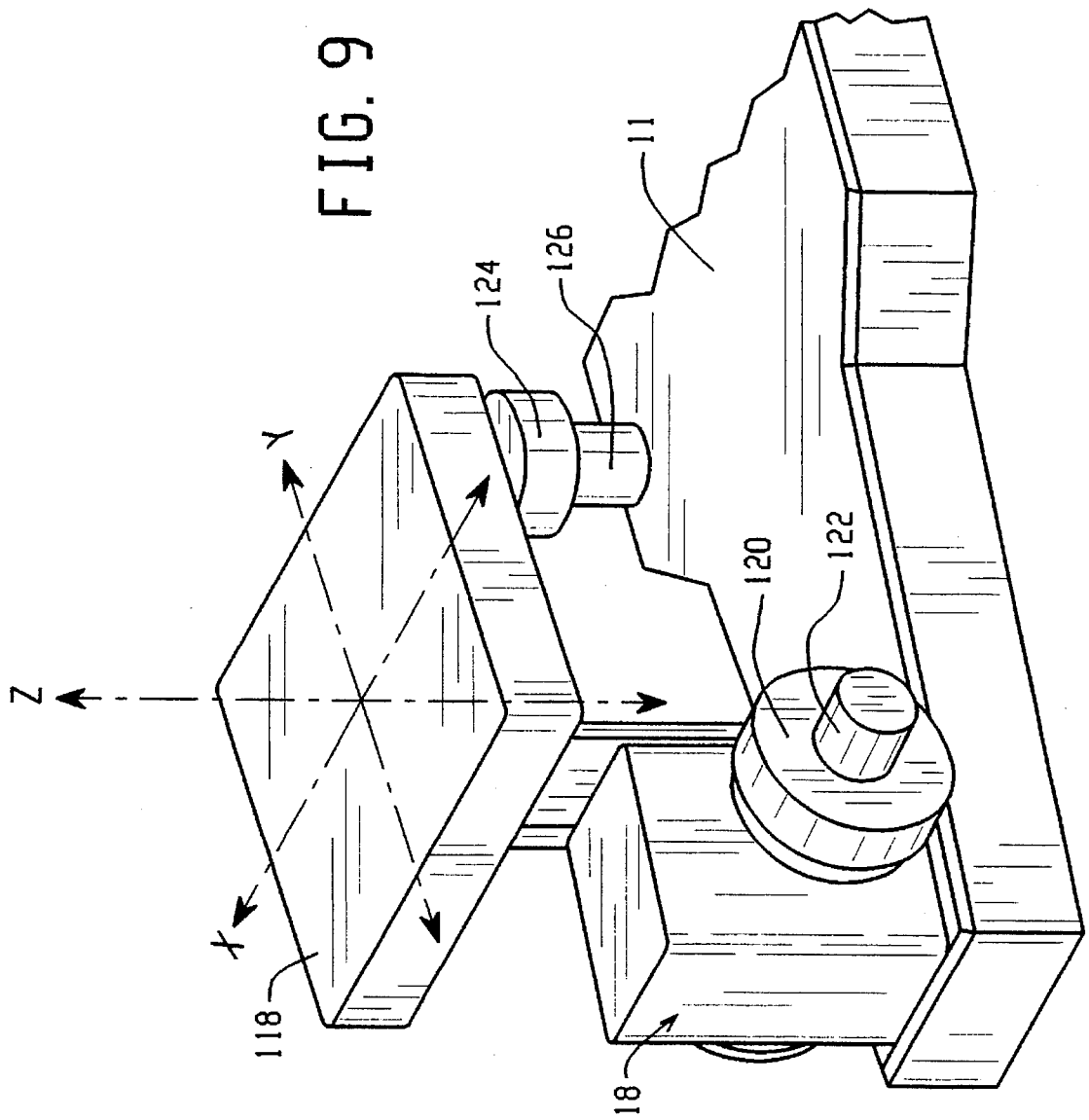

INFRARED MICROSPECTROMETER ACCESSORY

BACKGROUND OF THE INVENTION

The present invention relates generally to the field of microanalysis, particularly to the field of Fourier-transform-infrared microspectrometry, and specifically to reflection techniques of infrared microspectrometry. Spectroscopic analysis using radiant energy in the infrared region of the spectrum is a primary technique for chemical analysis. Since the introduction of commercial infrared microspectrometers, the advantages of being able to both view the sample area with a visible-light microscope and define microscopic areas for analysis by limiting the viewing field for spectral measurement has proven to be of great value. Infrared microspectrometer systems, disclosed in U.S. Pat. No. 4,877,747 to Donald W. Sting and Robert G. Messerschmidt, have been used for an ever-expanding range of applications. They have been used to detect and identify trace contaminants, to analyze multilayered composite structures such as packaging materials, to analyze micro-electronic devices, to establish phase distributions in polymeric materials, to identify inclusions in minerals, and so forth.

These microscope systems analyze samples in the nanogram to picogram weight range. The sampling area ranges from 100×100 micrometers ($\mu$m) to 10×10 $\mu$m. The goal is to analyze the smallest possible sampling area. This invention is based on the recognition that most microanalysis is performed on samples that are visible to the unaided eye. For these samples, the present microscope systems are too costly and too complex for the analyst. The infinity-corrected microspectrometer accessory of this invention uses infinity-corrected optics to produce a system without remote field apertures, and incorporates an integral video-imaging system for video microscopy. This system fills an important need in microanalysis, reduces the system's cost, and is easier for the analyst to use.

The microscope described in the Sting and Messerschmidt patent has been the standard configuration for infrared microspectroscopy. This established the need for both transmission and reflection capabilities and for remote-image-plane masks. At this time, all commercial microscopes use remote-image-plane masks to define sample areas.

A primary requirement of a true infrared microscope system for microspectrometry is that it should be able to perform transmission measurements and/or reflection measurements. Transmission infrared spectroscopy has been the primary mode for collecting spectral data. However, reflection techniques have advantages over transmission techniques because of the minimum requirements for sample preparation for reflection measurements. Reflection techniques make the analyses of samples much less expensive.

Reflection-only microspectrometer systems also greatly reduce the cost and complexity of a micro-sampling accessory. In microspectrometer systems that allow both transmission and reflection measurements, two optical systems have been required. One system delivers radiant energy to the sample and collects reflected radiant energy, while a second system is required to detect radiant energy transmitted through the sample. The dual functions of transmission and reflection greatly complicate the optical design.

Internal-reflection microspectroscopy provides certain advantages over both transmissive techniques and external reflection microspectroscopy, particularly in the ability to analyze thick samples. With the introduction of internal-reflection microspectrometry, as shown in U.S. Pat. No. 5,093,580 to Donald W. Sting, and U.S. Pat. No. 5,200,609 to Donald W. Sting and John A. Reffner (also known as attenuated total reflection microspectrometry or micro-ATR) reflection microspectrometry has gained even greater importance.

Prior to this invention, all micro-sampling accessories with viewing capabilities have used conventional microscope optics (in the form of an objective, an eyepiece, and a direct-viewing head) with an option of attaching either a photographic camera or a video camera. However, these accessories required additional optical elements so that the eyepiece and viewing head could be positioned at a convenient location. Provisions for attaching a photographic or video camera also added to the cost of the accessory. By eliminating a number of optical elements and other parts needed in earlier accessories to achieve the same capability, this invention simplifies and reduces the cost of the accessory.

Most samples analyzed by infrared spectroscopy are a microgram ($\mu$g) or larger in size. A $\mu$g of material is generally just barely visible, whereas most samples analyzed via infrared spectroscopy are detectable with the unaided eye. With this invention, these $\mu$g-sized samples may be analyzed easily via internal or external reflection, with little or no sample preparation. By microsamples, we mean samples or areas of large specimens that generally represent 0.05–50 $\mu$g of solid or liquid material. In this infinity-corrected microsampling accessory, the area of the sample analyzed is determined by the detector element's size, the detector optics, the source size, the source optics, and the objective optics. Commercially available Fourier-transform spectrometer benches have radiant-energy sources that are several millimeters in their smallest dimension. Since the source optics of commercial FT-IR spectrometers usually have focal lengths greater than the focal length of the objective lens, the image of the source on the sample is generally much larger than the projected size of the detector on the sample. In this invention, it is usually the detector size and its associated optics that determine the size of the sample being analyzed by the radiant energy. This is a unique feature of the infinity-corrected optical system of this invention. In all commercially-available infrared microspectrometer systems, field apertures are used to define the size of the sampling area. In this invention, the detector and source (together with associated optics) define the sampling area. This infinity-corrected system is further simplified, in comparison with presently available microspectrometer accessory systems, because the collimated radiant energy from the source and the radiant energy reflected from the sample, which is recollimated by the objective lens, can be directed along the optical path by plane mirrors, positioned at any of a number of positions along the optical path. The use of plane mirrors, and the freedom to select positions for these mirrors based on structural and manufacturing considerations, instead of the optical considerations which dictated the design of current instruments, make the accessory of this invention less expensive and more robust.

It is an object of the present invention to provide an infrared microspectrometer accessory that allows: (a) visual examination by an integrated video system, (b) external-reflection spectral analysis, and (c) internal-reflection spectral analysis.

Another object is to use infinity-corrected reflecting objectives both to provide a means for directing radiant energy onto a microscopic area and to allow visualization of the magnified image of the specimen through an integral video system.

A further object is to provide a simplified system for internal-reflection spectroscopy of microscopic samples with the same objective-lens used to view the microscopic sample. The internal-reflection element is inserted into the light path to allow internal-reflection spectral measurement.

Yet another object is to provide an internal-reflection element that reduces the need to control the angle of incident radiation by objective lens optical design.

A still further object of the present invention to provide a simplified system for detecting contact of a sample with an internal-reflectance element.

Other objects of this invention will be apparent from the following description, which is provided to enable any person skilled in the art to make and use the invention, and which sets forth the best mode contemplated by the inventors of carrying out their invention. Various modifications to the specific embodiment disclosed herein, within the general principles of the invention as defined herein, will be apparent to those skilled in the art.

BRIEF DESCRIPTION OF THE DRAWINGS

FIG. 7b is a bottom plan view of FIG. 7a.

FIG. 9 is a perspective view of the sample positioning assembly for the accessory of FIG. 1.

DETAILED DESCRIPTION

Figure 1:
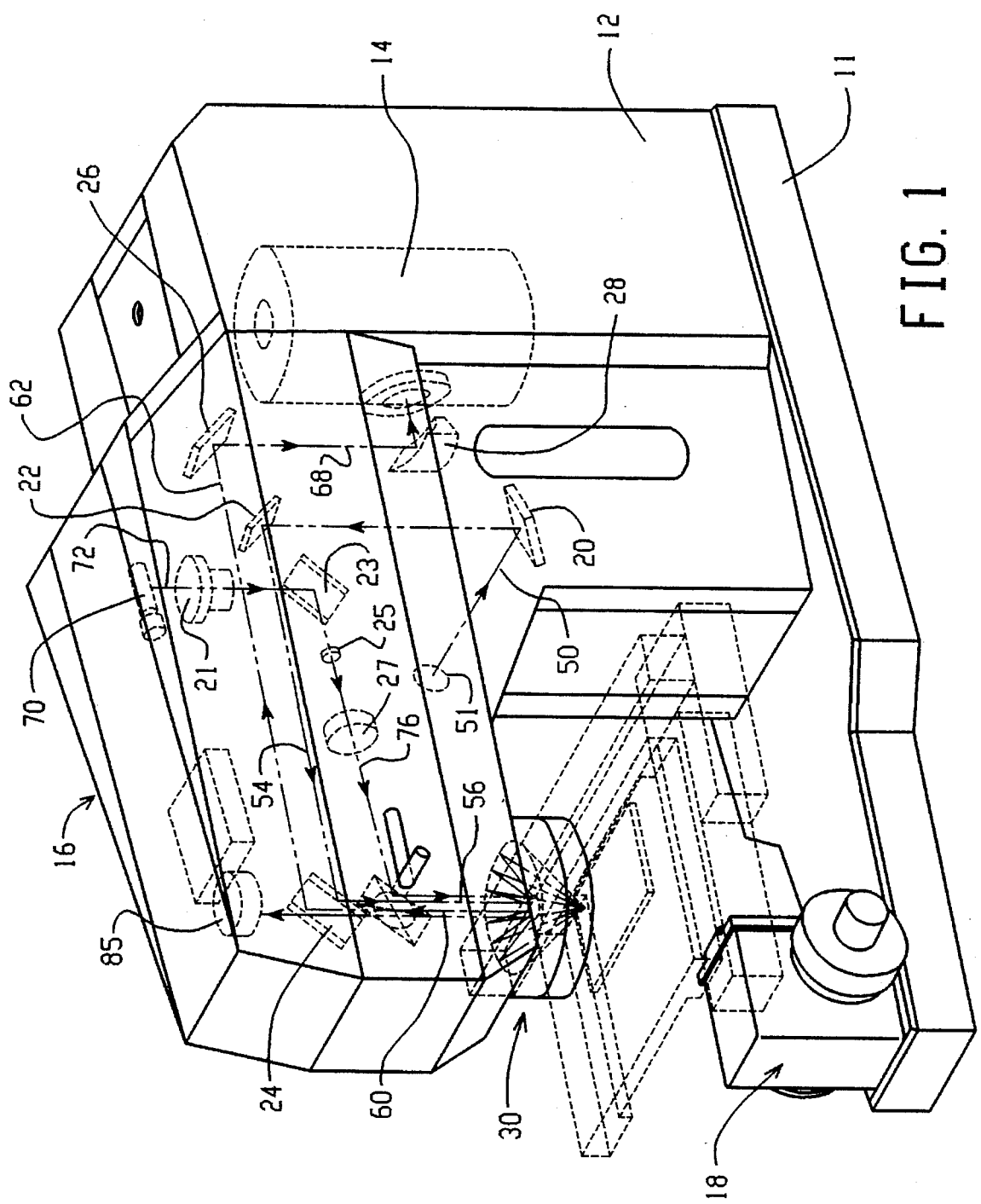
FIG. 1 is a perspective view, with a schematic illustration of the propagation of radiant energy, of an infinity-corrected reflectance microspectrometer accessory, with integrated video microscopy, embodying this invention.

FIG. 1 illustrates an infinity-corrected micro-sampling reflectance accessory embodying the principles of the present invention. Designed for use with a Fourier-transform infrared spectrometer, this accessory makes it possible, with simple, rapid and precise adjustments, to perform visual examinations as well as external-reflection and internal-reflection spectral analyses.

For visualization of the magnified image, this accessory has a source of visible radiation that is collimated and directed onto the sample through a series of lenses, mirrors, and beam-splitters that (together) provide a means of illumination. The visible radiant energy reflected from the sample is collected and recollimated by the objective lens, and then passes through a beam splitter to allow the collimated beam of visible radiant energy to be directed to a video detector means. A lens means focuses the visible radiant energy onto the active surface of video camera. The electronic image recorded by the video camera is relayed to a monitor or is video-inputted into a computer system. In the preferred embodiment, the video image is presented to a video-input terminal to a computer, and a digitized image is created for viewing the live video, for storing, for video enhancement, or for recording of video images of microscopic samples. The integral video system, combined with the infinity-corrected objective lens, greatly simplifies the design of this infrared microspectrometer accessory.

The visible-radiant-energy beam-splitter and the infrared-radiant-energy mirror directing the radiation to the objective lens are mounted on a movable support, and may be shifted into and out of the beam paths.

For internal and external reflection spectral analyses, the base 11 of the accessory supports a housing 12, in which an infrared radiant energy detector 14 is mounted. An arm assembly 16 is mounted upon and extends forward from the upper part of housing 12. A sample support and positioning assembly 18 is mounted on base 11 beneath the front end of arm 16.

The collimated infrared beam 50 from a Fourier-transform-infrared spectrometer (as used herein, it should be understood that, as is customary in the spectrometric art, the term "collimated" means substantially or nearly collimated) enters the accessory via an opening 51. Generally, any spectrometer system producing a nearly-collimated beam-including Nicolet Magna Models 550, 750 or 850; BioRad Model FTS-40; and Perkin-Elmer Models 1600, 2000 and the Paragon—may be used as a source of radiant energy.

Figure 2:
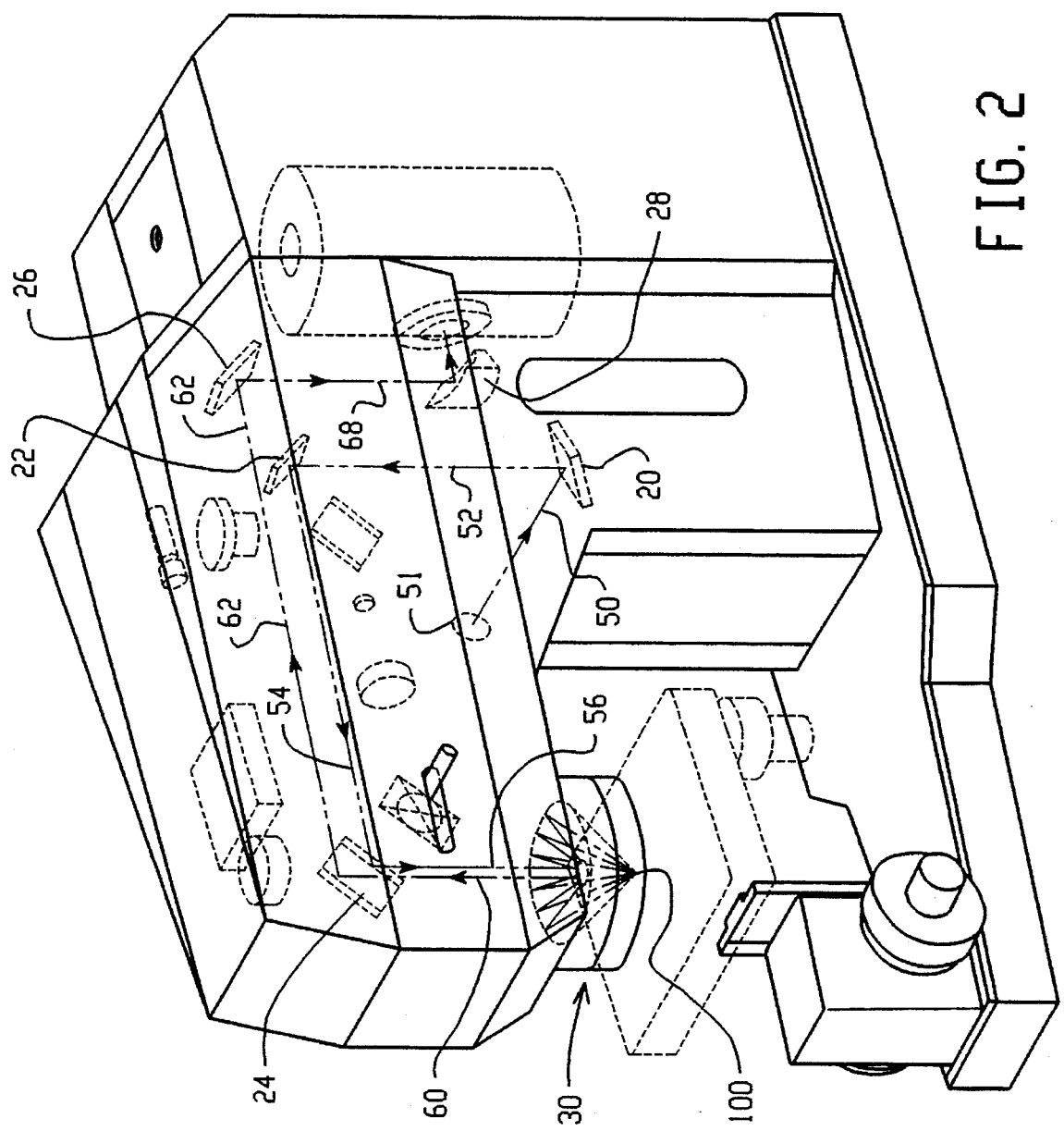
FIG. 2 is a schematic illustration, from the same vantage point as FIG. 1, of the propagation of radiant energy in the internal-reflection and external-reflection modes of operation of the instrument shown in FIG. 1.
Figure 7A:
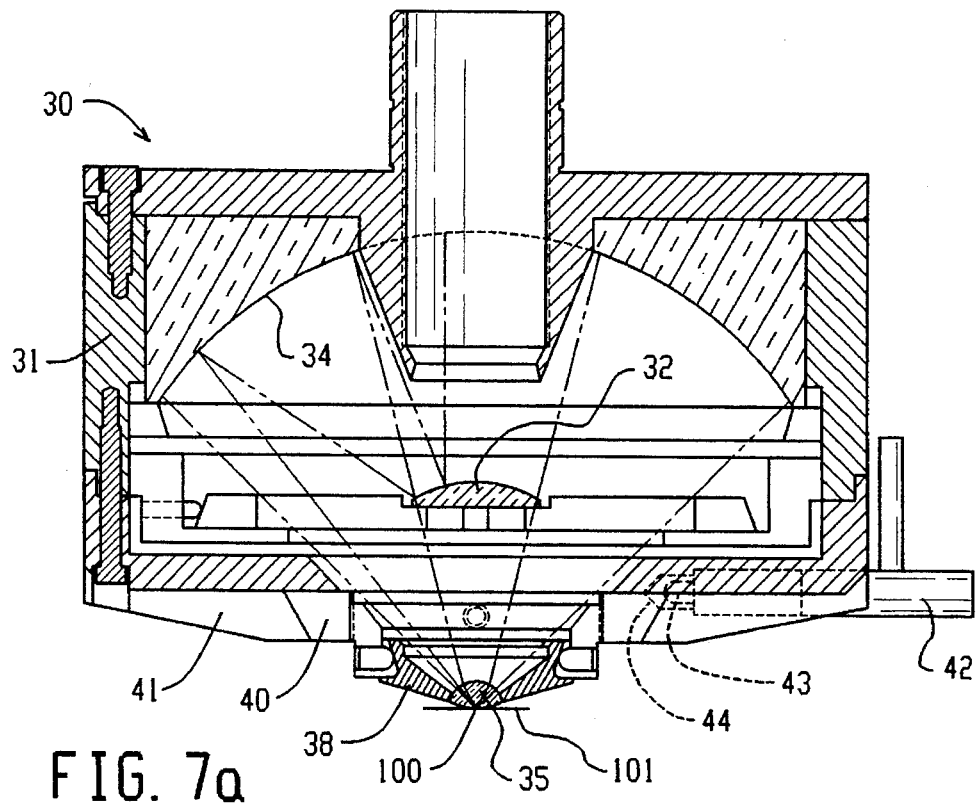
FIG. 7a is a cross-sectional view of an objective lens for performing video viewing and examination, as well as internal-reflection and external-reflection spectral analysis.
Figure 7B:
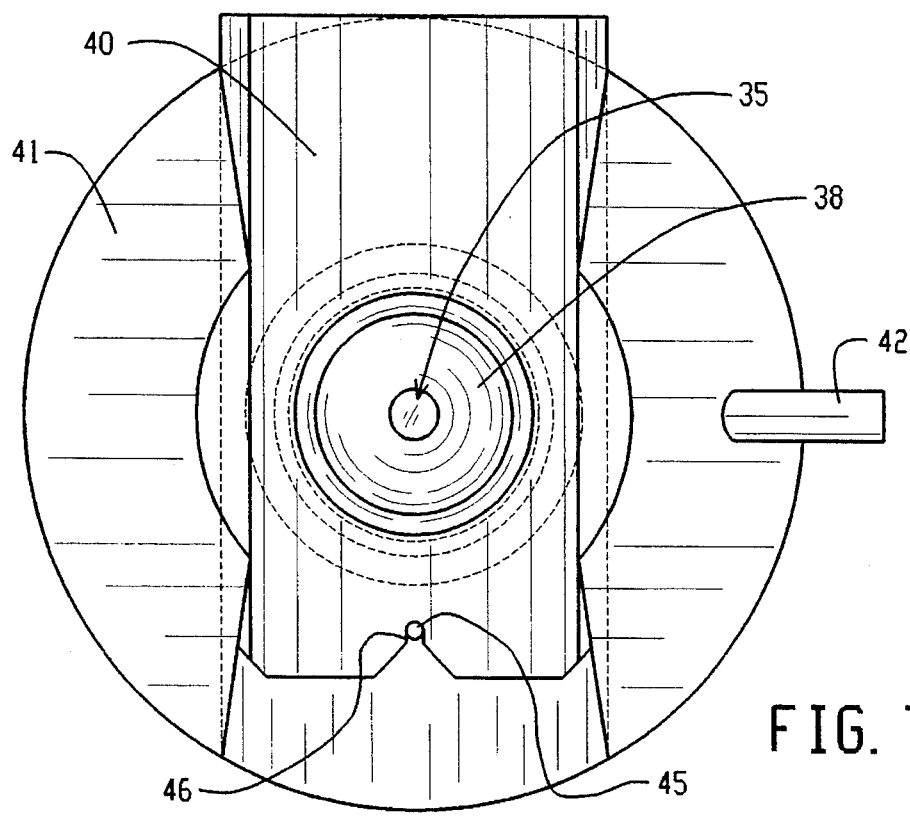
Figure 8:
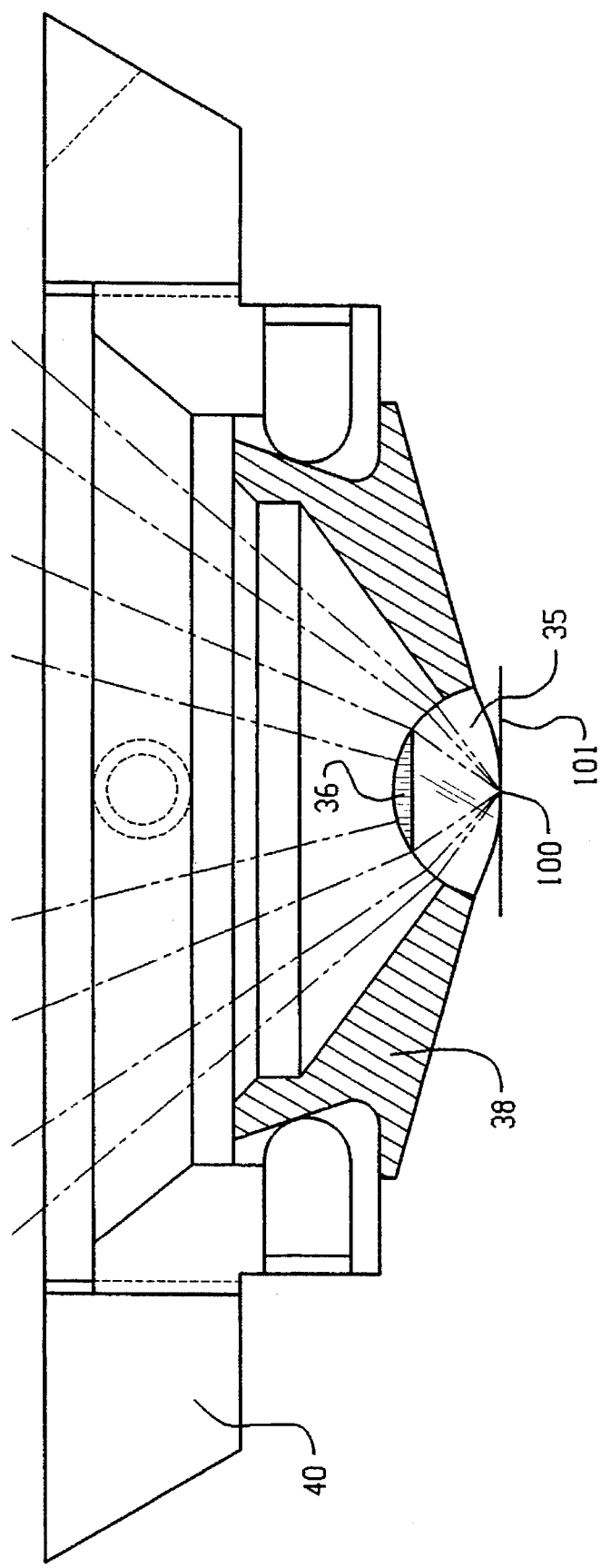
FIG. 8 is an enlarged cross-sectional elevation view of the end of the objective lens shown in FIG. 7, with an internal-reflection element or IRE positioned beneath it.

As may be best seen in FIG. 2, the collimated beam 50 is directed by a series of plane or flat mirrors 20, 22 and 24 through an objective lens 30, shown in more detail in FIGS. 7 and 8, to a sample 100, best seen in FIG. 8. Collimated beam 50 is reflected by mirror 20, as collimated beam 52, to mirror 22. Collimated beam 52 is reflected by mirror 22, as collimated beam 54, to mirror 24. Collimated beam 54 is reflected by mirror 24, as collimated beam 56, to objective lens 30. As shown in FIG. 7a, objective lens 30 is comprised of a convex reflecting element 32 and a concave reflecting element 34, whose surfaces and spacings are such that they produce a focused beam at the plane where a sample 100 is located, which is indicated by line 101 in FIG. 8. The objective lens 30 must produce a cone of radiant energy whose angle of incidence onto the sample, i.e., the angle between the surface normal and the incident radiation at the optical interface between the internal reflection element or IRE 35 (best seen in FIG. 8) and sample 100, which may be between about 10° and about 50°, and is more typically between about 20° and about 45°, exceeds the critical angle for the optical interface. As shown in FIG. 8, a mask 36 may be placed upon IRE 35 to ensure that the incident angle of radiation upon the IRE is above the minimum for the IRE material. This allows the objective lens to be used with a wider range of IRE materials. The mask may be applied by vapor deposition of an opaque layer of a metal such as aluminum or gold. For reasons of economy, and because it is widely used by optics manufacturers for plating mirrors, aluminum is preferred.

Mirror 22, shown in FIGS. 1 and 2, functions as a remote-aperture beam-splitter in a collimated beam. The aperture beam-splitter is a critical element in the optical design of this microspectrometer accessory. It functions to allow radiant energy from the source to be directed into one-half of the aperture of the objective lens. Objective lens 30 directs the energy incident upon one-half of the aperture of this infinity-corrected objective system onto the sample. Radiation reflected from the sample returns through the other half of the aperture of objective lens 30, which recollimates the radiation.

In internal-reflection analyses, the incident radiation falls on internal reflection element 35. The internal reflection element is removed during external-reflection analyses and video viewing, and the incident radiation falls directly on sample 100. The illustrated objective lens 30 can accommodate IREs of varying refractive indices. The restriction of the angular cone of radiation striking the interface between the IRE 35 and sample 100 is controlled by the numerical aperture of the objective lens 30 and a mask 36 (FIG. 8) on the IRE itself.

IRE 35 is mounted in a fixture 38, which in turn is mounted in a slide 40, which is supported for sliding motion normal to the plane of FIG. 7a by a slide support 41. Slide support 41 is secured to the housing 31 of the objective lens 30. Slide 40 and fixture 38 contain mechanisms that allow the centering and height adjustments of the internal-reflection element 35.

For external-reflection measurements slide 40, fixture 38, and IRE 35 are removed from the radiant energy path, allowing the radiant energy to come to focus at the plane 101 of the sample 100. Slider 40 and IRE 35 are removed from the radiant energy path for both the view mode shown in FIG. 6 and the external-reflection mode shown in FIG. 4.

IRE 35, fixture 38, and slide 40 are locked into place with a locking fastener 42, which can be a spring-loaded piece having a tip 43 that extends into a v-notch 44 and thereby secures the 35, fixture 38, and slide 40 in place. The IRE 35 is aligned with the focal point of the objective lens 25 in one direction via slide 40 and slide support 41. The IRE 35 is aligned with the focal point of the objective lens 30 in the other direction via a peg 45 that extends into a notch 46.

In its preferred embodiment, the sample is viewed via the integrated video system prior to infrared spectral measurement. After positioning the desired sample area in the viewing field, the IRE is moved into the light path.

Figure 10A:
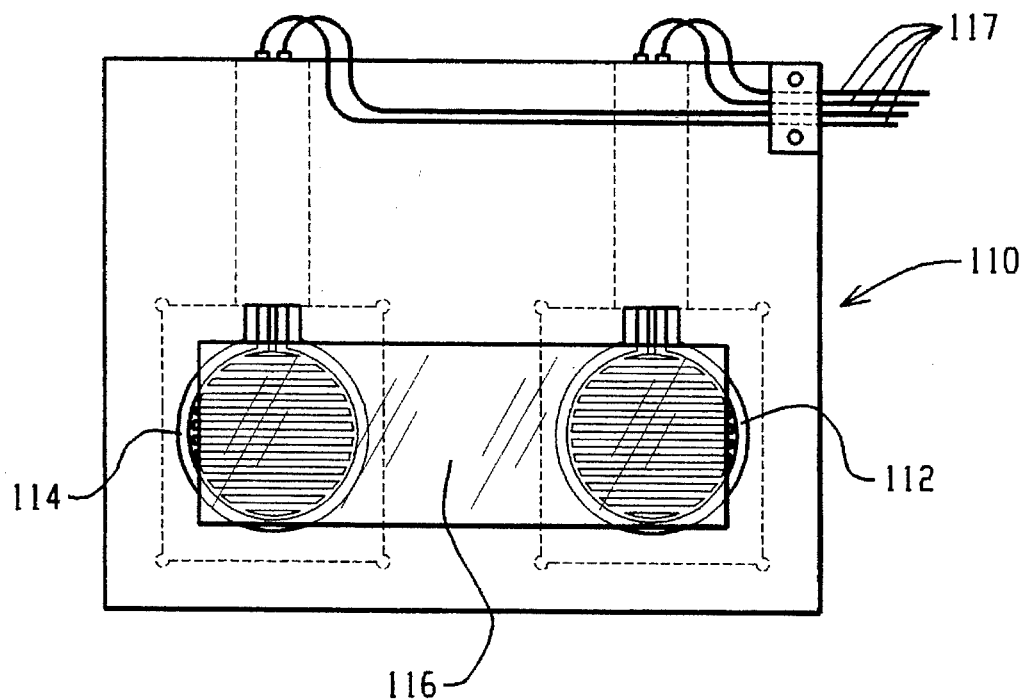
FIGS. 10a and 10b are top and bottom plan views of a sensor plate, mounted on the positioning assembly shown in FIG. 8, that indicates when a sample has been properly positioned for internal-reflection spectrometry.
Figure 10B:
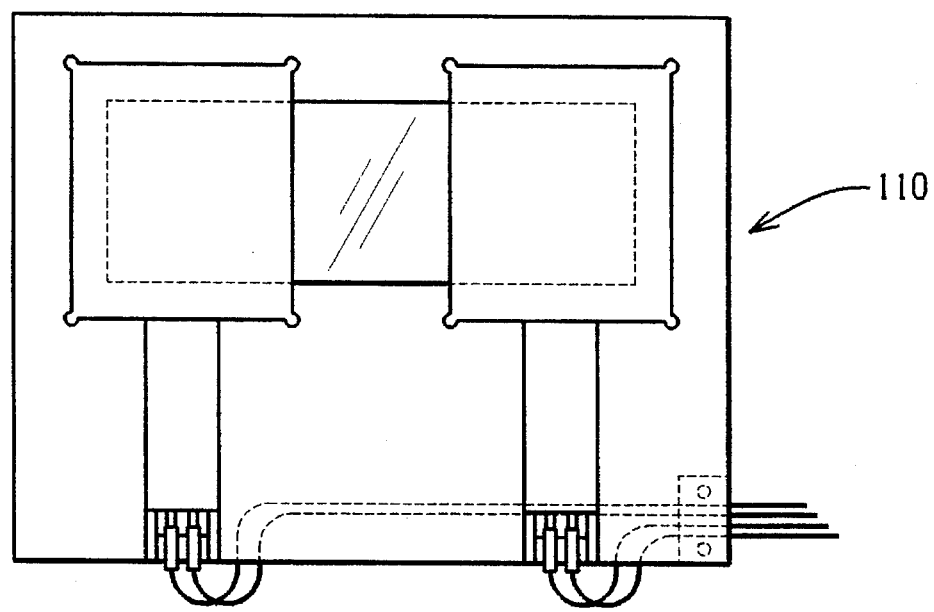

The contact of sample 100 with IRE 35 is detected by an electronic sensor assembly, shown generally as 110 in FIGS. 10a and 10b. Electronic sensor 110 includes a pair of resistive force sensors 112, 114. A slide 116, upon which the sample 100 is placed, sits on sensors 112 and 114. These sensors are connected via leads 117 to electronic circuitry, which reacts to changes in the forces detected by the sensors 112, 114. This electronic means alerts the operator to the fact that initial contact has been made.

This alert is preferably accomplished through an indicator light that comes on when contact between the sample 100 and the IRE 35 is made. If the sample is further pressed against the IRE, the contact-sensor warning will remain illuminated until a certain force is reached, wherein a second warning alert, such as another illuminated warning, is actuated.

Preferably, the force-sensing resistors 112, 114 are placed beneath the slide 120 and sample 100. This is the simplest arrangement, and the force applied to the slide and sample by the sensor assembly helps to insure good contact between the sample and IRE. Triangulation of the forces applied by the two sensors and the reactive force by the sample insure positive contact.

The electronic sensor assembly 110 sets upon an adjustable platform 118 in the sample support and positioning assembly 18, which is shown in more detail in FIG. 9. Platform 118 provides efficient and convenient means of moving the sample to locate desirable areas for analysis or for moving from one sample to another for rapid, repetitive analysis.

One knob 120 provides coarse adjustment of the platform along the Z-axis. A second knob 122, coaxial with knob 120, provides fine adjustment in the same direction. Knobs 124 and 126 provide, respectively, precise movements by the platform 118 and sample 100 in the x and y directions.

The internal-reflectance element can be formed from Ge-As-Se glass (e.g., Ge-As-Se glass sold under the trademark "AMTIR," which is owned by Amorphous Materials, Inc., Garland, Tex.), arsenic-modified selenium glass (SeAs), cadmium sulfide (CdS), cadmium telluride (CdTe), germanium (Ge), indium antinomide (InSb), KRS-5, thalium bromide-thalium iodide (TlBr-TlI), silicon (Si), silver bromide (AgBr), silver chloride (AgCl), thalium bromide (TrBr), zinc selenide (ZnSe), zinc sulfide (ZnS), diamond, and zirconia ($ZrO_2$), among others. The preferred embodiment of this invention would be to use silicon as the internal-reflection element. The IRE, preferably has a diameter of 1–3 mm; however, larger or smaller radii of curvature could be used.

Radiation reflected from the sample 100 passes back through the IRE 35 to the objective lens 30, which reflects this radiation as a collimated reflected beam 60 to mirror 24. Objective lens 30 is infinity corrected. In other words, the curvatures of the mirror lens elements 32 and 34 and their spacing are adjusted so that the focussing properties of the lens are such that a nearly-collimated beam will be brought to a point focus. Conversely, any point illuminated in the sample plane will produce a nearly collimated beam of radiant energy emerging from objective lens 30. This infinity-corrected design provides both radiant-energy spectroscopy and visible-radiant-energy imaging with a greatly simplified and less expensive system, because limitations on positioning the various optical elements that direct the radiation to the objective lens and from the objective lens to the detector, and the accuracy with which these elements had to be positioned in prior accessories, is greatly reduced.

The reflected radiation collected by the objective lens is collimated and returns in a path parallel to the incident radiation. Mirror 24 reflects collimated reflected beam 60, as collimated reflected beam 62, toward mirror 22. The reflected beam 62 travels along the upper half of the path from mirror 24 toward mirror 22 and strikes mirror 26. Because of the physical displacement of the reflected ray path, this radiation will not strike the aperture beam splitter's mirror but (instead) passes toward the detector means. Therefore, half of the aperture receives radiant energy; if the sample were a perfect mirror, all of this radiation would then be passed to the detector. Hence, the aperture-splitting beam-splitter 22 would allow an efficiency of 50% to be achieved. This is at least a factor of 2 greater than earlier designs of beam-splitters (known as refracting beam-splitters or reflecting beam-splitters). Because beams 50, 52, 54, 56, 60, 62, and 68 are collimated (or substantially so), aperture-splitting beam-splitter 22 (and mirrors 20, 24, 26 and 28) may be placed in a wide range of locations. Position is not critical. The distances between mirrors 20 and 22, between mirrors 22 and 24, between mirrors 24 and objective lens 30, between mirrors 24 and 26, and between mirrors 26 and 28 are not critical, thereby allowing flexibility in their positioning and reducing the cost of the system of the present invention. Again, this simplifies the design of the optical system, reducing costs and improving the accessory's convenience of operation.

Because the objective lens is improperly-designed for collimated radiation, the reflected beam 62 is nearly collimated and passes over mirror 22 to mirror 26. From mirror 26, the beam is reflected, as collimated reflected beam 68, onto mirror 28. Mirror 28 is a focusing means for directing the beam into detector 14, which generates an electrical signal corresponding to the intensity of the radiation in the reflected beam 68. The electrical signal produced by the detector means is then sent to the spectrometer for Fourier-transform analysis.

The detector 14 schematically illustrated in the drawings is a standard commercial Nicolet MCTA detector with a detector element size of 0.25 mm. While this detector is preferred, we do not wish to limit ourselves to it alone; other detectors are available with smaller element sizes, as are detectors of infrared radiant energy with different types of detection (such as folometers and/or photo-conductive types of detectors). The mercury-cadmium-telluride (MCT) detector is a photovoltaic detector.

The detector element's geometry is a very important aspect of the infinity-corrected system, since it plays an important role in determining the size of the sample area being analyzed. This is an important point because what we have recognized in this invention is that the source size and the detector size may be used as definers of the sample area. The source optics, the objective lens, and the detector optics are chosen so that the desired size of sampling area is obtained. This means that we can fix the optical geometry for a specific minimum sample area (making the system easier for the analyst to use) and can reduce the cost of the system, compared with the cost of adjustable-aperture systems used in all current microspectrometer systems.

Figure 5:
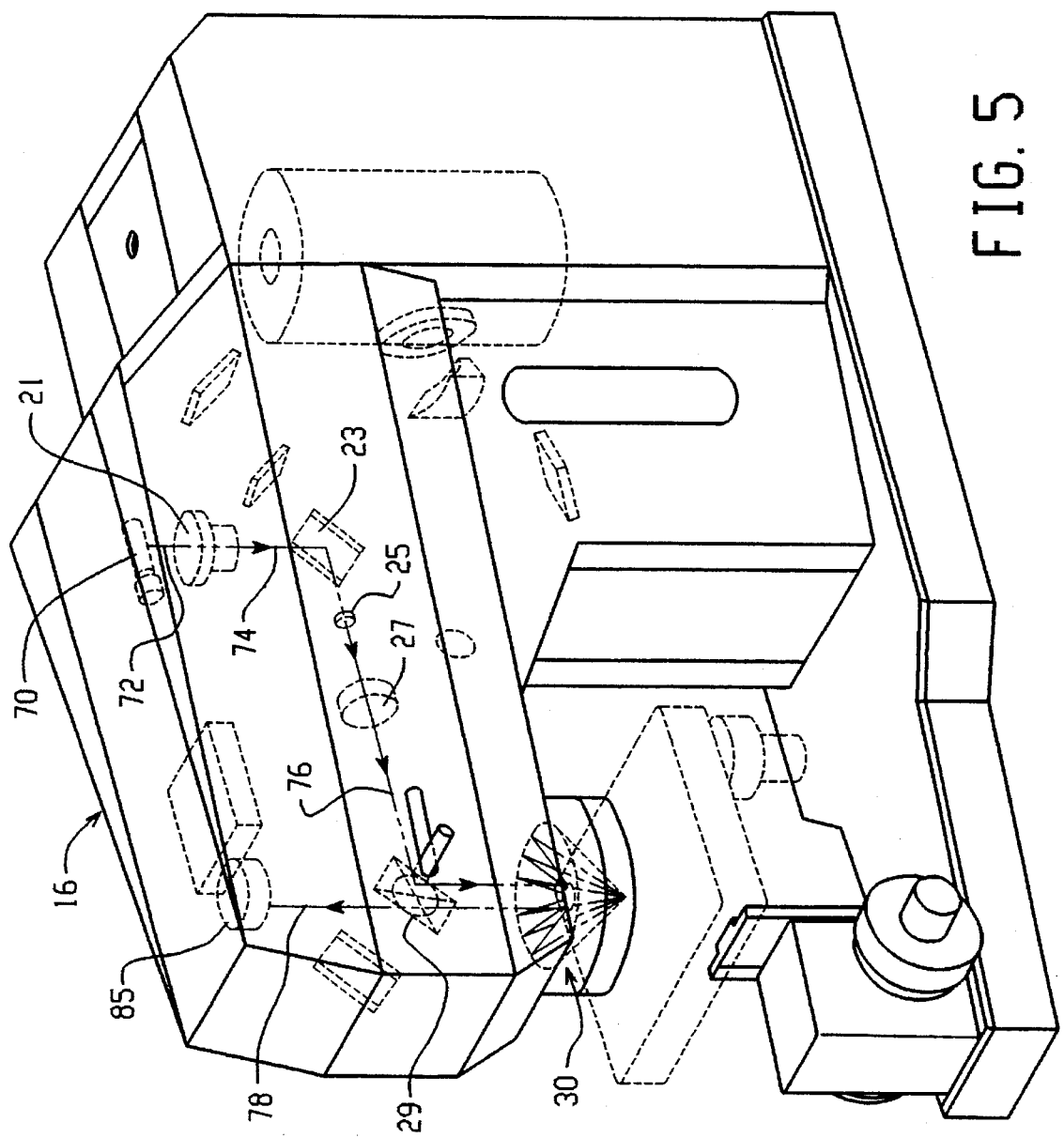
FIG. 5 is a schematic illustration, from the same vantage point as FIG. 1, of the propagation of visual radiant energy when the accessory of FIG. 1 is used for video viewing or examination of samples.
Figure 6:
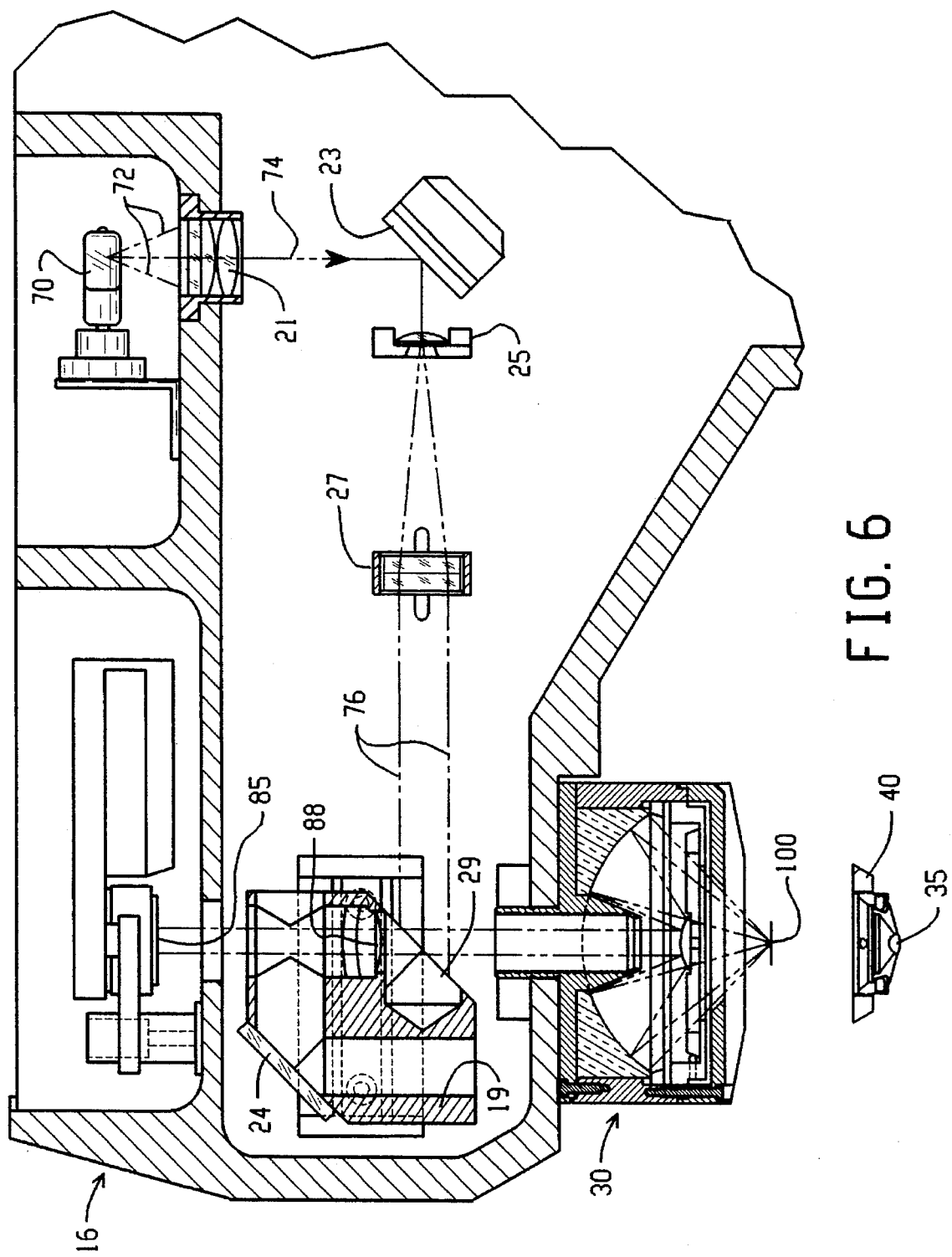
FIG. 6 is a partial cross-sectional side elevation view of the same process.

FIGS. 5 and 6 illustrate the view mode of the accessory of the present invention is shown. Lamp 70 is a source of visible radiant energy 72, which passes through refracting lens element 21. The refracted radiant energy 74 from lens element 21 is reflected by a flat mirror 23 through lens 25 to collimating lens 27, which collimates the refracted radiant energy 74 and directs a beam of collimated radiant energy onto a beam-splitter 29. The beam-splitter 29, which is a visible radiant energy beam-splitter, is moved into the path for viewing in the view mode and out of the light path for spectral measurement in the internal-reflection and external-reflection modes. The beam of collimated visible radiant energy 76 is directed from the beam-splitter element 29 down through objective lens 30 to the sample 100. In the view mode, the IRE 35 is moved out of the path of the light incident on the sample 100 by the slide 40 shown in FIGS. 7 and 8.

On reflection from the sample 100, the reflected visible radiant energy is recollimated by the objective lens 30, as was the infrared radiation in the internal reflection mode discussed above. The recollimated beam passes through beam splitter 29, and then travels toward the location where mirror 24 is positioned in the IR modes. Mirror 24 is moved out of the path of the beam 78 of recollimated radiant energy 78 when the system is in the viewing mode. The beam 78 travels up through a lens element 88, which focusses the collimated beam 78 on the video camera element 85. The video element 85 and associated electronics generate an electronic signal corresponding to the image on the video element 85. The electronic signal corresponding to the image is then transmitted to either a video monitor or a computer system.

Lenses 21, 25, 27, and 88 can each comprise one individual lens or a number of optically coupled lenses. The relative positions of these lenses are critical only to the extent that the light 72 from source 70 is converted into a collimated beam 76, which is directed through beam splitter 29. Additional lenses might be used and one or more of the mirrors and lenses shown in FIGS. 5 and 6 might be removed if the characteristics and positions of the other lenses are changed to compensate. Because the beam 76 of visible radiant energy is collimated, the distance between lens 27 and beam splitter 29 can vary widely, giving further flexibility to the configuration of the components of the system. The relative position of lens 88 is critical only to the extent that the collimated radiation 128 is focused onto the video element 85 in such a fashion that a video signal corresponding to the image of the sample can be generated by associated electronics.

Figure 3:
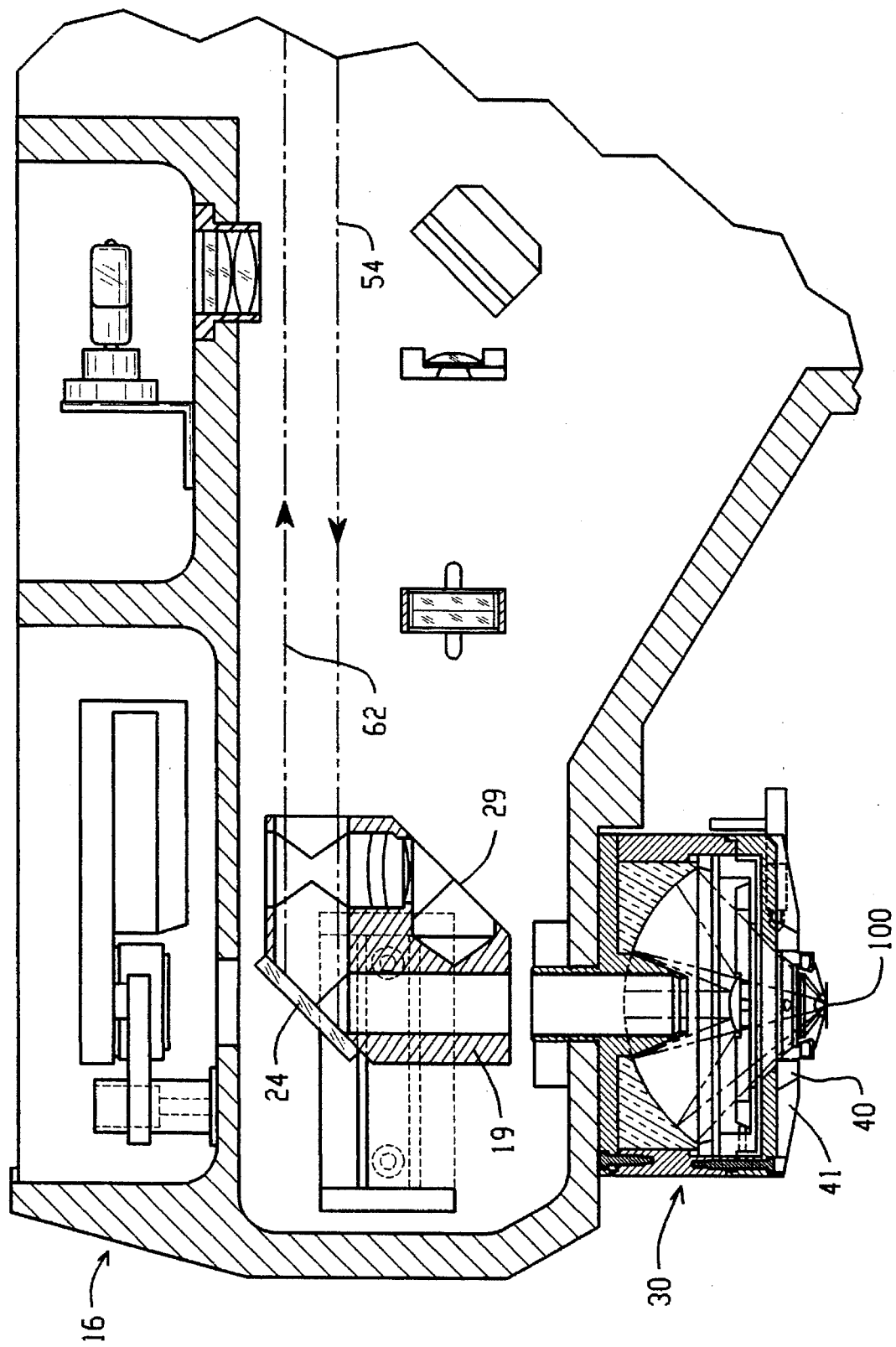
FIG. 3 and 4 are partial cross-sectional side elevation views illustrating, respectively, internal-reflection and external-reflection spectrographic examinations.
Figure 4:
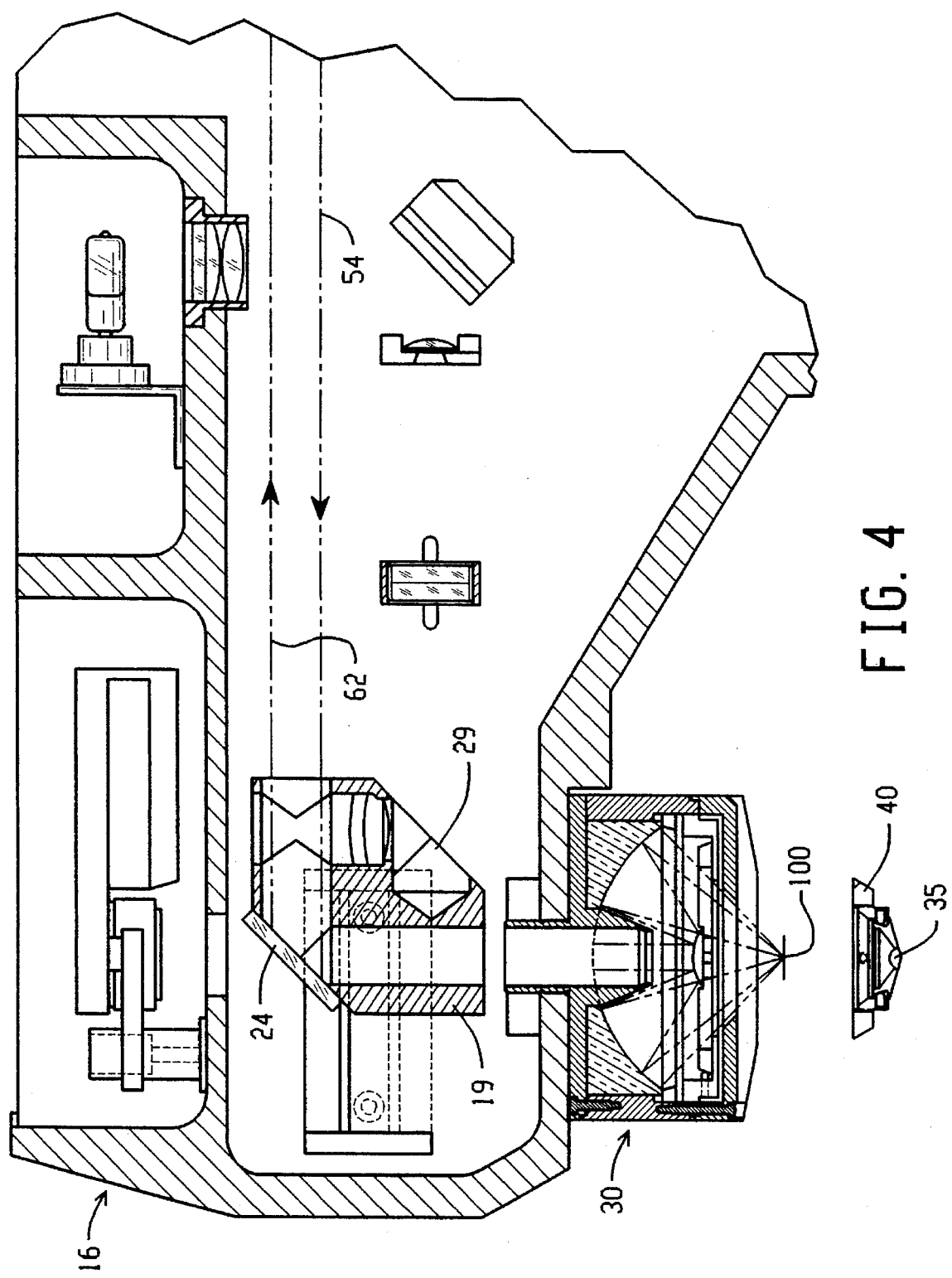

As mentioned above, both mirror 24 and visible radiant energy beam splitter 29 are mounted so that they can be moved into and out of the path of radiant energy. Preferably, as shown in FIGS. 3, 4 and 6, both mirror 24 and beam splitter 29 are mounted on a movable support assembly 19, mounted for reciprocal movement within arm assembly 16. When the movable support assembly is moved towards the front of arm assembly 16, as shown in FIG. 6, the beam splitter 29 directs the beam 76 of collimated radiant energy from collimator 27 to objective lens 30. Reflected radiation passes through the beam splitter and past mirror 24, which has been moved out of the path.

When the movable support assembly moves toward the rear of arm assembly 16, as shown in FIGS. 3 and 4, beam splitter 29 moves out of the radiant energy path, mirror 24 moves in. In this position, mirror 24 directs radiant energy to the objective lens, and directs reflected radiation to detector 14 for spectral analysis. Thus, the movable support assembly, with mirror 24 and beam splitter 29, provides a quick, inexpensive and precise mechanism for switching back and forth from the viewing mode to one of the spectral analysis modes.

The infinity-corrected imaging system of this invention offers a significant advantage over optical systems currently being used in micro spectrometer systems. In the case of this invention, the infinity-corrected system allows the use of plain mirrors to carry the radiant energy from the infrared spectrometer to the objective, thereby reducing the cost and simplifying the optical design of the system. This simplification greatly reduces the costs of this micro-sampling accessory. Viewing in combination with the integrated video system is a further cost-reducing feature. Combining the elements of infinity correction with integrated video microscopy for both internal and external reflection makes this a unique system. It provides a fixed, rigid design that enhances its overall performance and reliability for microanalysis.

This invention also allows the analyst to perform external-reflection spectrometry, by removing the IRE 35 from the radiant-energy beam path, as shown in FIG. 4. External-reflection measurements include specular reflection, diffuse reflection, and reflection-absorption. Specular reflection is the first surface reflection of a material. It produces characteristic absorption spectra that can be best analyzed by transforming the reflectivity to absorption spectra through the Kramers-Kroenig transformation. Specular reflection is preferred when the sample has a smooth, reflective surface. Diffuse reflection is light that has been scattered at random angles and has traversed through portions of the material, wherein radiant energy is absorbed by the sample. The infinity-corrected Schwarzschild objective produces an incident beam of radiant energy that can be scattered through all angles of the collection aperture of the objective lens. This light can then be transmitted to the detector means for a transform analysis. In diffuse reflection, the sample is generally dispersed in a non-absorbing matrix (such as KBr, KCl, or sulfur). The diluted samples produce higher-quality diffuse-reflectance spectra. Reflection-absorption spectra are produced by thin films of absorbing material that are on the surface of a metallic reflector. The incident radiant energy passes through the film to the metal surface. At the metal surface, the radiant energy is specularly reflected, passing through the thin film a second time. The reflected radiation is collected by the objective and is transmitted to the detector through the optical means. Since the radiant energy passes through the sample twice, this form of external-reflection spectroscopy is sometimes referred to as double-pass reflection.

Since, in the preferred embodiment, the user is able to combine both video-microscopy viewing of the sample and radiant-infrared-absorption spectral analysis in both external and internal-reflection modes, the invention has a wide range of applications. Droplets of polymer solution can be evaporated onto a mirror surface and the thin polymer film analyzed by reflection-absorption. Small quantities of drugs may be placed on a glass microscope slide and analyzed by internal-reflection spectroscopy, producing the ATR spectrum of the pharmaceutical material. Thick polymer sheets may be placed directly on the stage of the microsampling accessory and may be analyzed with no sample preparation via internal-reflection spectroscopy. Thick droplets of viscous liquids may be analyzed spectroscopically by specular reflection. The protective coatings on beverage containers may be analyzed directly by reflection-absorption spectroscopy. Materials separated by thin-layer chromatography may be analyzed on zirconia plates by diffuse-reflection spectroscopy.

Those skilled in the art will readily appreciate that numerous changes may be made in the specific embodiment described above within the scope of this invention, which is defined by the following claims.

We claim:

1. An analytical accessory with means for internal-reflection spectrometry, external-reflection spectrometry and video viewing of samples, comprising:

a source of collimated infrared radiation;

first optical means for directed a collimated beam of said infrared radiation to a remote aperture beam splitter;

said remote aperture beam splitter being adapted to direct a collimated beam of said radiation to an infinity corrected objective lens so that said radiation passes through one-half of the aperture of said objective lens;

means to position a sample at a focal point of said lens, whereby said infrared radiation is focussed on said sample, and radiation reflected from said sample is recollimated by said infinity corrected objective lens;

said infinity corrected objective lens and said first optical means being adapted to direct a collimated beam of said recollimated radiation to a focusing means, which focuses said radiation on a spectral detector adapted to generate an electrical signal corresponding to the intensity of said recollimated radiation;

a source of visible radiant energy, means for collimating said energy, and second optical means for directing a collimated beam of said visible radiant energy to said infinity corrected objective lens;

said infinity corrected lens being adapted to focus said visible radiant energy on a sample, and to recollimate visible radiant energy reflected from said sample;

said infinity corrected objective lens and said second optical means being adapted to direct a collimated beam of said recollimated visible radiant energy from said objective lens to a video sensor adapted to generate an electronic signal corresponding to an image on said video sensor.

2. An analytical accessory in accordance with claim 1, wherein:

said first optical means comprises a first optical element and means to move said optical element out of the path of said collimated infrared radiation; and said second optical means comprises a second optical element and means to move said second optical element out of the path of said visible radiant energy.

3. An analytical accessory in accordance with claim 2, further comprising a movable optical element mount, said first optical element and said second optical element being mounted on said optical element mount and positioned so that said mount can move said first optical element into the path of said collimated infrared radiation, and move said second optical element out of the path of visible radiant energy, by movement in one direction; and can move said first optical element out of the path or said infrared radiation, and move said second optical element into the path of visible radiant energy, by movement in another direction.

4. An analytical accessory in accordance with claim 3, wherein said second optical element is a visible radiant energy beam splitter.

5. An analytical accessory in accordance with claim 4, wherein said first optical element is a mirror.

6. An analytical accessory in accordance with claim 1, further comprising means for positioning an internal reflection element between said objective lens and said sample and in contact with said sample, whereby radiation focussed on said sample by said lens passes through said internal reflection element, strikes said sample, is reflected from said sample through said internal reflection element to said lens, and is recollimated by said lens.

7. An analytical accessory as disclosed in claim 6, further comprising a movable support, said internal reflection element being mounted on said movable support, whereby said internal reflection element may be moved out of the path of radiation from said lens to said sample to permit external reflection spectral analysis.

8. A spectrometer with integrated viewing capability comprising:

a detector adapted to generate an electrical signal corresponding to the intensity of radiant energy striking the detector;

a source of substantially collimated radiant energy;

first optical means for directing a collimated beam of radiant energy to an infinity-corrected objective lens having a convex reflecting surface and a concave reflecting surface;

said convex surface being designed and positioned to reflect said beam toward said concave surface, and said convex surface and said concave surface being designed and positioned to bring said collimated beam to a point focus;

means for supporting a material to be inspected, analyzed, or inspected and analyzed, substantially at said point focus, whereby radiation is reflected from said material and is recollimated by said infinity corrected objective lens and directed at said first optical means, said first optical means being adapted to direct a collimated beam of said recollimated radiation to focusing means, which focuses said radiation on said detector;

a source of visible radiant energy;

means for substantially collimating said visible radiant energy;

second optical means for directing a collimated beam of radiant energy to said objective lens and for directing collimated reflected visible radiant energy from said lens to a video sensor.

9. A spectrometer as disclosed in claim 8, including means to direct reflected collimated radiation to different locations.

10. A spectrometer in accordance with claim 9 wherein said means for directing said reflected beam comprises at least one movably mounted optical element and means to move said element into and out of said reflected beam.

11. A spectrometer in accordance with claim 10, further comprising an internal-reflection element and means for movably mounting said internal-reflection element so that a sample may be placed in contact with said internal-reflection element at a focal point of said objective lens for internal-reflective spectrographic analysis, and said internal reflection element may be moved away from said focal point for external reflective spectrographic analyses or visual inspection or examination.

12. An accessory for an analytical instrument, comprising:

means for supporting a material to be inspected, analyzed, or inspected and analyzed;

optical means for directing a substantially collimated beam of radiant energy to an infinity corrected objective lens having a convex reflecting surface and a concave reflecting surface;

said convex surface being designed and positioned to reflect said beam toward said concave surface, and said concave surface being designed and positioned to reflect said beam toward said material;

said convex surface and said concave surface being designed and positioned to bring said beam to a point focus at said material, whereby radiation is reflected from said material and is refocused by said concave surface and said convex surface as a substantially collimated beam of reflected radiation directed at said optical means;

said objective lens and said optical means being adapted to direct a substantially collimated beam of said reflected radiation to a focusing means, which focuses said radiation on a detector means for spectroscopic analysis.

13. An accessory in accordance with claim 12 wherein said optical means further comprises a movably mounted optical element and means to move said element into and out of said collimated beam of reflected radiation.

14. An accessory in accordance with claim 12 including second optical means to receive a beam of substantially collimated radiation and direct said beam of substantially collimated radiation to a video sensor adapted to generate an electronic signal corresponding to the image in said video sensor.

15. An accessory in accordance with claim 14 wherein said means for directing said reflected beam comprises a movably mounted optical element and means to move said element into and out of said reflected beam.

16. An accessory in accordance with claim 12, further comprising an internal-reflection element; and means for movably mounting said internal-reflection element so that a sample may be placed in contact with said internal-reflection element at a focal point of said objective lens for internal-reflective spectrographic analysis, and said internal reflection element may be moved away from said focal point for external reflective spectrographic analyses or visual inspection or examination.

17. An accessory for an analytical instrument, comprising:

means for supporting a material to be inspected, analyzed, or inspected and analyzed;

optical means for directing a substantially collimated beam of radiant energy to an objective lens having a convex reflecting surface and a concave reflecting surface;

said convex surface being designed and positioned to reflect said beam toward said concave surface, and said concave surface being designed and positioned to reflect said beam toward said material;

said convex surface and said concave surface being designed and positioned to bring said beam to a point focus at said material, whereby radiation is reflected from said material and is refocused by said concave surface and said convex surface as a substantially collimated reflected beam directed at said optical means;

further comprising an internal-reflection element and sample positioning means adapted to press said sample against said internal-reflection element, and said sample positioning means comprises force sensing means adapted to produce an electrical signal corresponding to the force with which the sample is pressed against the internal reflection element.

18. Apparatus in accordance with claim 17 comprising an internal-reflection element, said means for positioning said internal-reflection element, said positioning means being adapted to move said internal-reflection element out of the path of radiation from said objective lens to said sample, whereby external-reflection spectral analyses and video examinations of said sample may be performed.

19. An internal-reflection element for a spectrometer comprising a body of a material that is transparent to infrared radiation, said body having a first surface adapted to contact a sample, a curved surface adapted to receive incident radiation and to transmit radiation reflected from said sample at said first surface, and an opaque material applied to a portion of said curved surface to ensure that the incident angle of radiation passing through said body of material is above the minimum for said material.

20. An internal-reflection element in accordance with claim 19 wherein said opaque material is aluminum.

21. An internal-reflection element in accordance with claim 20 wherein said aluminum is applied to said body by vapor deposition.

* * * * *